US009170182B2

(12) United States Patent
Gibson et al.

(10) Patent No.: US 9,170,182 B2
(45) Date of Patent: Oct. 27, 2015

(54) METHOD OF FATIGUE TESTING A COMPONENT

(71) Applicant: ROLLS-ROYCE PLC, London (GB)

(72) Inventors: Grant Gibson, Buckinghamshire (GB); Andrew Jonathan Leggett, Derby (GB)

(73) Assignee: ROLLS-ROYCE PLC, London (GB)

( * ) Notice: Subject to any disclaimer, the term of this patent is extended or adjusted under 35 U.S.C. 154(b) by 250 days.

(21) Appl. No.: 13/857,549

(22) Filed: Apr. 5, 2013

(65) Prior Publication Data

US 2013/0298693 A1    Nov. 14, 2013

(30) Foreign Application Priority Data

May 10, 2012 (GB) .................................. 1208153.5

(51) Int. Cl.
*G01L 1/22* (2006.01)
*G01N 3/34* (2006.01)

(52) U.S. Cl.
CPC .................. *G01N 3/342* (2013.01); *G01N 3/34* (2013.01); *G01N 2203/0016* (2013.01)

(58) Field of Classification Search
CPC .. G01N 3/34; G01N 2203/0016; G01N 3/342
See application file for complete search history.

(56) References Cited

U.S. PATENT DOCUMENTS 4,748,854 A  * 6/1988 Rao .................................. 73/799
6,615,671 B1   9/2003 Carstensen et al.

FOREIGN PATENT DOCUMENTS

EP          1 602 914 A2    12/2005
SU          1642330 A1      4/1991

OTHER PUBLICATIONS

Gabb et al., "The Effects of Hot Corrosion Pits on the Fatigue Resistance of a Disk Superalloy," NASA/TM 2009-215629, Aug. 2009.
Search Report issued in British Patent Application No. GB1208153.5 issued Aug. 23, 2012.

* cited by examiner

*Primary Examiner* — Lisa Caputo
*Assistant Examiner* — Brandi N Hopkins
(74) *Attorney, Agent, or Firm* — Oliff PLC

(57) ABSTRACT

A method of fatigue testing a component comprising the steps of machining a channel of predetermined depth and predetermined width in a surface of a component, applying a salt solution into the channel in the surface of the component and heating the component to a suitable temperature to evaporate the solvent from the salt solution to deposit the salt in the channel in the surface of the component, placing the component in an atmosphere containing air and sulphur dioxide at a predetermined temperature for a predetermined period of time to precondition the grain boundaries, and fatigue testing the component. The method is useful for determining the fatigue life of gas turbine engine discs or gas turbine engine rotor blades particularly the firtree shaped disc posts or the firtree shaped rotor blade roots.

28 Claims, 4 Drawing Sheets

METHOD OF FATIGUE TESTING A COMPONENT

The present invention relates to a method of fatigue testing a component, particularly to a method of fatigue testing of a superalloy component and more particularly to a method of fatigue testing of a nickel based superalloy component.

Fatigue testing is carried out on new components to determine their fatigue life and in the case of used components fatigue testing is carried out to determine their remnant, or remaining, fatigue life. The fatigue testing may be used to assess the fatigue life after a component has been subjected to hot corrosion, this a known corrosion mechanism which occurs in nickel based superalloys at high temperatures.

A paper entitled "The Effect of Hot Corrosion Pits on the Fatigue Resistance of a Disk Superalloy" by T P Gabb, J Telesman, B Hazel, D P Mourer, NASA/TM-2009-215629 discloses pre-corroding cylindrical specimens of a nickel based superalloy, a nickel based superalloy used to produce gas turbine engine turbine discs, to assess the influence of corrosion on the remnant fatigue life. Some of the cylindrical specimens. were shot peened. A mixture of sulphur containing salts was applied to the specimens and they were exposed in air at 704° C. for 8 and 24 hours within a resistance heating furnace in order to produce accelerated hot corrosion damage. Then low cycle fatigue testing was carried out on the specimens.

A problem with these tests is that the salt level used in the tests is an order of magnitude to high and therefore the morphology of corrosion features produced during the tests is incorrect at representing the edge of bedding channels seen during service of actual components, e.g. nickel based superalloy gas turbine engine turbine discs. In addition the method is not suitable for investigating the fatigue life of complex geometry components, e.g. the surfaces of firtree, or dovetail, shaped slots, or posts, in a turbine disc, because the method is not controlled and the mixture of sulphur containing salts runs off the areas of the component that are of interest and collects on, and produces corrosion in, the areas of the component that are not of interest.

Accordingly the present invention seeks to provide a novel method of fatigue testing a component which reduces, preferably overcomes, the above mentioned problems.

Accordingly the present invention provides a method of fatigue testing a component comprising the steps of:— a) machining a channel of predetermined depth and predetermined width in a surface of a component, b) applying a salt solution into the channel in the surface of the component and heating the component to a suitable temperature to evaporate the solvent from the salt solution to deposit the salt in the channel in the surface of the component, c) placing the component in a corrosive atmosphere for a predetermined period of time at a predetermined temperature to precondition the grain boundaries, and d) fatigue testing the component.

Step b) may comprise heating the component to 200° C. and applying salt solution at a rate of 0.25 $\mu g/cm^2/hr$ to 10 $\mu g/cm^2/hr$.

The corrosive atmosphere in step c) may comprise air and sulphur dioxide. The predetermined period of time in step c) may be 50 to 500 hours. The predetermined period of time in step c) may be 300 hours. The predetermined temperature in step c) may be 600° C. to 750° C.

Step d) may comprise fatigue testing in air. Step d) may comprise fatigue testing in a corrosive atmosphere. Step d) may comprise fatigue testing in air and sulphur dioxide.

Step d) may comprise fatigue testing to determine the remnant life of the component.

Step d) may comprise repeatedly applying a salt solution into the channel in the surface of the component and heating the component to a suitable temperature to evaporate the solvent from the salt solution to deposit the salt in the channel in the surface of the component and placing the component in a corrosive atmosphere at a predetermined temperature for predetermined periods of time while fatigue testing the component to determine the remnant life of the component.

Step d) may comprise applying a salt solution into the channel in the surface of the component and heating the component to a suitable temperature to evaporate the solvent from the salt solution to deposit the salt in the channel in the surface of the component and placing the component in a corrosive atmosphere at a predetermined temperature and stopping the fatigue testing after predetermined numbers of cycles, examining the component and predicting the rate of growth of the channel after a given number of fatigue cycles.

The corrosive atmosphere may comprise air and sulphur dioxide. The predetermined temperature may be 600° C. to 750° C.

The component may comprise a specimen having the shape of a gas turbine engine rotor disc post or a rotor blade root. The component may have a firtree shape or a dovetail shape. Step a) may comprise machining the channel in an edge of bedding region of a tooth of the firtree shape rotor disc post or rotor blade root.

Step a) may comprise electro-discharge machining the channel of predetermined depth and predetermined width in a surface of a component.

Step d) may comprise low cycle fatigue testing or high cycle fatigue testing.

The present invention will be more fully described with reference to the accompanying drawings, in which.

Figure 1:
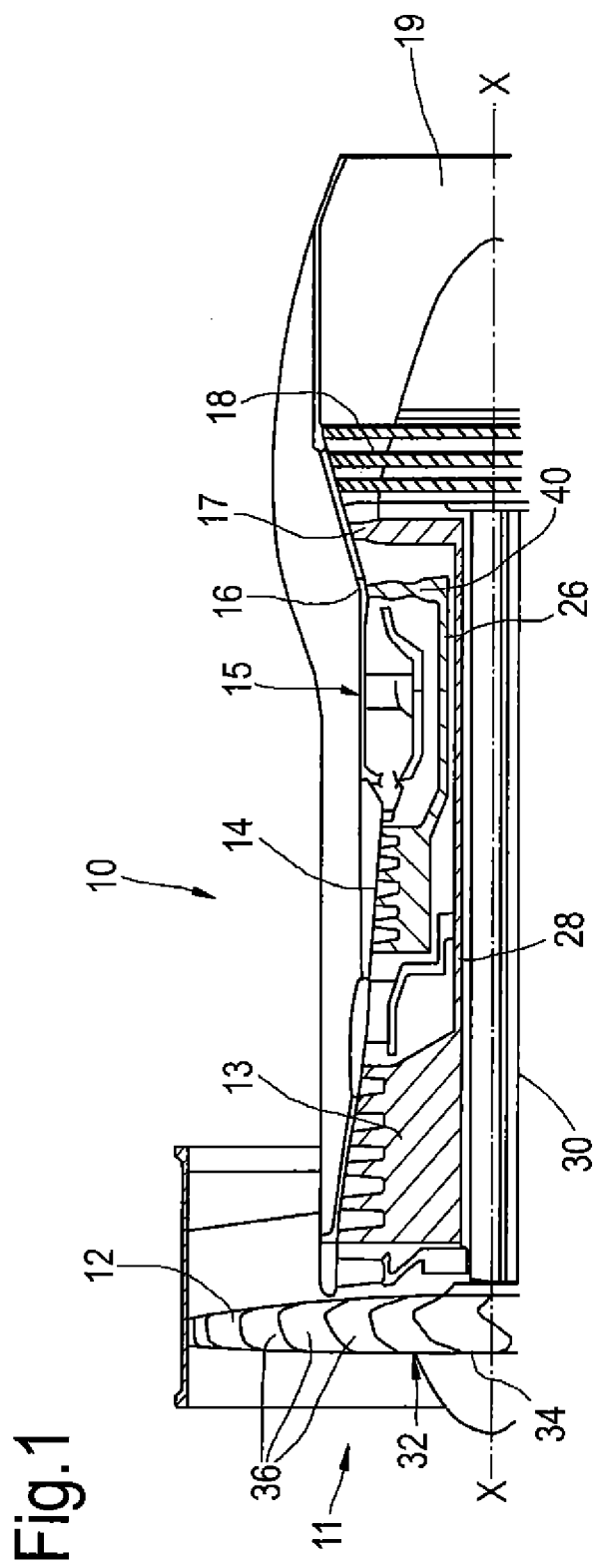
FIG. 1 is a cross-sectional view through a turbofan gas turbine engine.

A turbofan gas turbine engine 10, as shown in FIG. 1, comprises in flow series an intake 11, a fan 12, an intermediate pressure compressor 13, a high pressure compressor 14, a combustor 15, a high pressure turbine 16, an intermediate pressure turbine 17, a low pressure turbine 18 and an exhaust 19. The high pressure turbine 16 is arranged to drive the high pressure compressor 14 via a first shaft 26. The intermediate pressure turbine 17 is arranged to drive the intermediate pressure compressor 14 via a second shaft 28 and the low pressure turbine 19 is arranged to drive the fan 12 via a third shaft 30. In operation air flows into the intake 11 and is compressed by the fan 12. A first portion of the air flows through, and is compressed by, the intermediate pressure compressor 13 and the high pressure compressor 14 and is supplied to the combustor 15. Fuel is injected into the combustor 15 and is burnt in the air to produce hot exhaust gases which flow through, and drive, the high pressure turbine 16, the intermediate pressure turbine 17 and the low pressure turbine 18. The hot exhaust gases leaving the low pressure turbine 18 flow through the exhaust 19 to provide propulsive thrust. A second portion of the air bypasses the main engine to provide propulsive thrust.

Figure 2:
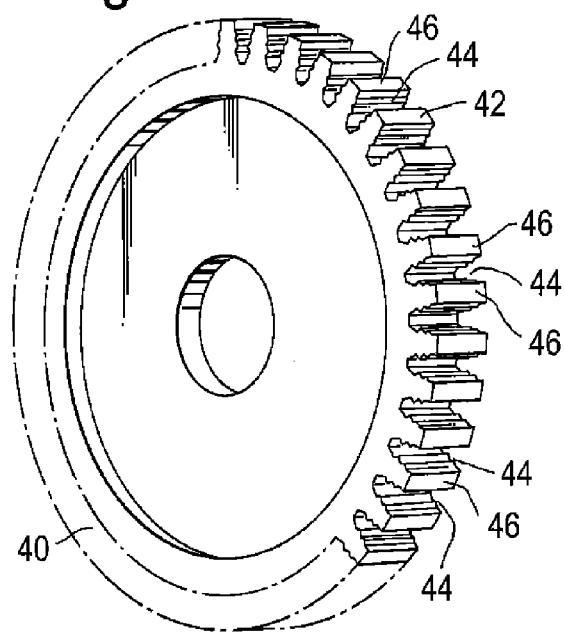
FIG. 2 is an enlarged perspective view of a turbine disc of the turbofan gas turbine engine shown in FIG. 1.
Figure 3:
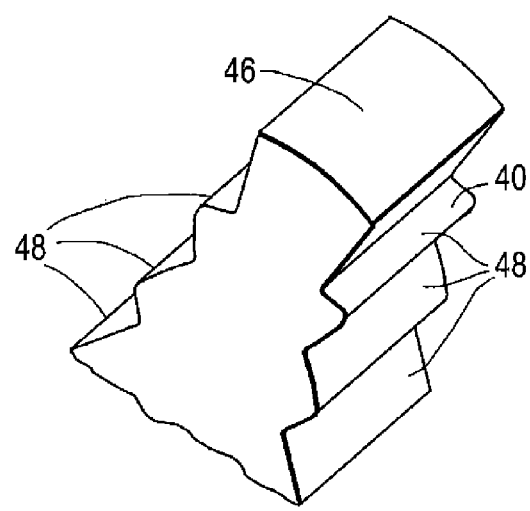
FIG. 3 is an enlarged perspective view of a disc post of the turbine disc in FIG. 2.

The high pressure turbine 16 comprises a turbine disc 40, as is shown in FIG. 2. The turbine disc 40 comprises a plurality of equi-circumferentially spaced slots 44 in the rim 42 of the turbine disc 40. The slots 44 are either firtree shaped or dovetail shaped and are defined by defined between equi-circumferentially spaced correspondingly shaped disc posts 46. One of the disc posts 46 is shown more clearly in FIG. 3 and the disc post 46 comprises a number of radially spaced teeth 48 on opposite radially spaced sides of the disc post 46. The turbine disc 40 comprises a nickel based superalloy, for example RR1000 which consists of 18.5 wt % cobalt, 15 wt % chromium, 5 wt % molybdenum, 2 wt % tantalum, 3.6 wt % titanium, 3 wt % aluminium, 0.5 wt % hafnium, 0.06 wt % zirconium, 0.027 wt % carbon, 0.015 wt % boron and the balance nickel plus incidental impurities.

Figure 4:
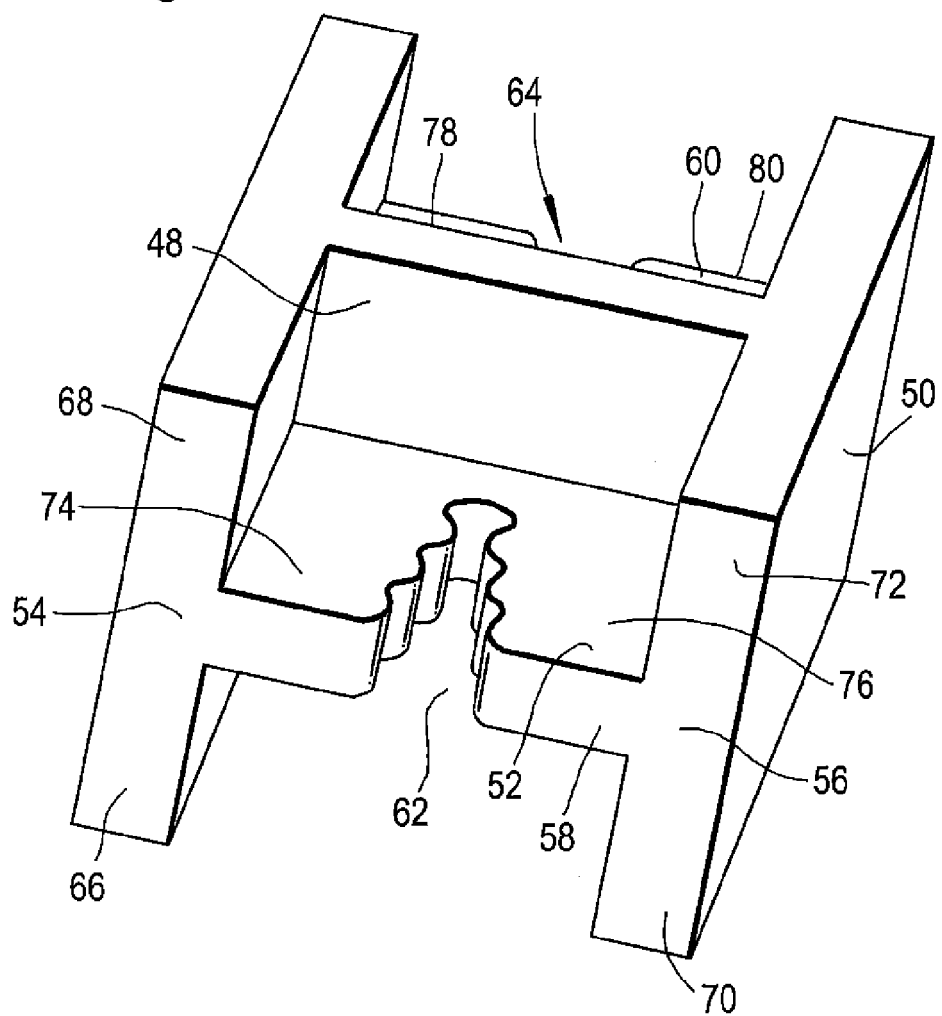
FIG. 4 is a perspective view of a disc post specimen corresponding to two adjacent disc posts in FIG. 3.

In order to determined the fatigue life of the turbine disc 40 and in particular to determine the fatigue life of a disc post 46 of the turbine disc 40 a nickel based superalloy specimen 50, as shown in FIG. 4, having a shape corresponding to that of two adjacent nickel based superalloy disc posts 46 is produced.

The specimen 50 is generally H-shaped in cross-section, as seen in FIG. 4, and comprises a first member 52 which has a first end 54, a second end 56, a first edge 58 and a second edge 60. The first edge 58 has a first firtree shaped slot 62 and the second edge 60 has a second firtree shaped slot 64. The first end 54 has flanges 66 and 68 extending laterally away from the first member 52 and the second end 56 has flanges 70 and 72 extending laterally away from the first member 52. The portions 74 and 76 of the first member 52 between the first slot 62 and the first and second ends 54 and 56 respectively correspond to disc posts. The portions 78 and 80 of the first member 52 between the second slot 64 and the first and second ends 54 and 56 respectively correspond to disc posts.

A channel 84 of predetermined depth D and predetermined width W is machined in a surface 82 of the specimen 50. A salt solution is supplied into the channel 84 in the surface 82 of the specimen 50 and the specimen 50 is heated to a suitable temperature to evaporate the solvent from the salt solution to deposit the salt in the channel 84 in the surface 82 of the specimen 50. The specimen 50 is placed in an atmosphere containing air and sulphur dioxide for a predetermined period of time at a suitable temperature to precondition the grain boundaries of the specimen 50. The predetermined period of time of preconditioning is related to the amount of damage that is required to be produced in the specimen 50. Generally, the longer the predetermined period of time the greater the degree of corrosion damage produced in the specimen 50.

A suitable salt consists of 98% sodium sulphate ($Na_2SO_4$) and 2% sodium chloride (NaCl), but other suitable mixtures of sodium sulphate and sodium chloride may be used and other suitable salts may be used. The salt solution is supplied into the channel 84 at a rate of 0.25 µg/cm²/hr to 10 µg/cm²/hr for example 1.5 µg/cm²/hr every 50 hours for the duration of the test in order to ensure that the salt is not used up. The salt is used up during the corrosion of the specimen and so more salt is supplied to replace the salt used. The specimen 50 is heated to a temperature of 200° C. to evaporate the solvent.

A suitable atmosphere of air and sulphur dioxide to precondition the grain boundaries of the specimen 50 consists of approximately 300 volume parts per million (vppm) of sulphur dioxide but other suitable amounts of sulphur dioxide may be used. The temperature to precondition the grain boundaries of the specimen 50 is in the range 600° C. to 750° C. in order to replicate type II hot corrosion. The most favourable temperature to precondition the grain boundaries of the specimen 50 is 700° C. The specimen 50 is maintained in the atmosphere containing air and sulphur dioxide for example for a time of 300 hours.

Figure 5:
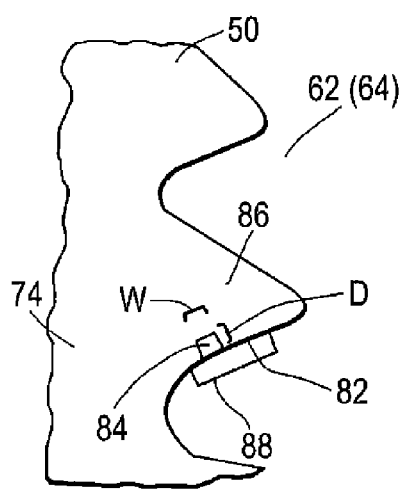
FIG. 5 is cross-sectional view through a part of the disc post specimen shown in FIG. 4.

The channel 84 may be machined into the surface 82 of the specimen 50 at an edge of bedding region 88 of a tooth 86 of the firtree shape specimen 50, as shown in FIG. 5. The channel 84 is machined into the surface 82 of the specimen 50 by electro-discharge machining to produce a channel 84 of predetermined depth D and predetermined width W. However, other suitable machining methods may be used to machine the channel 84.

Figure 7:
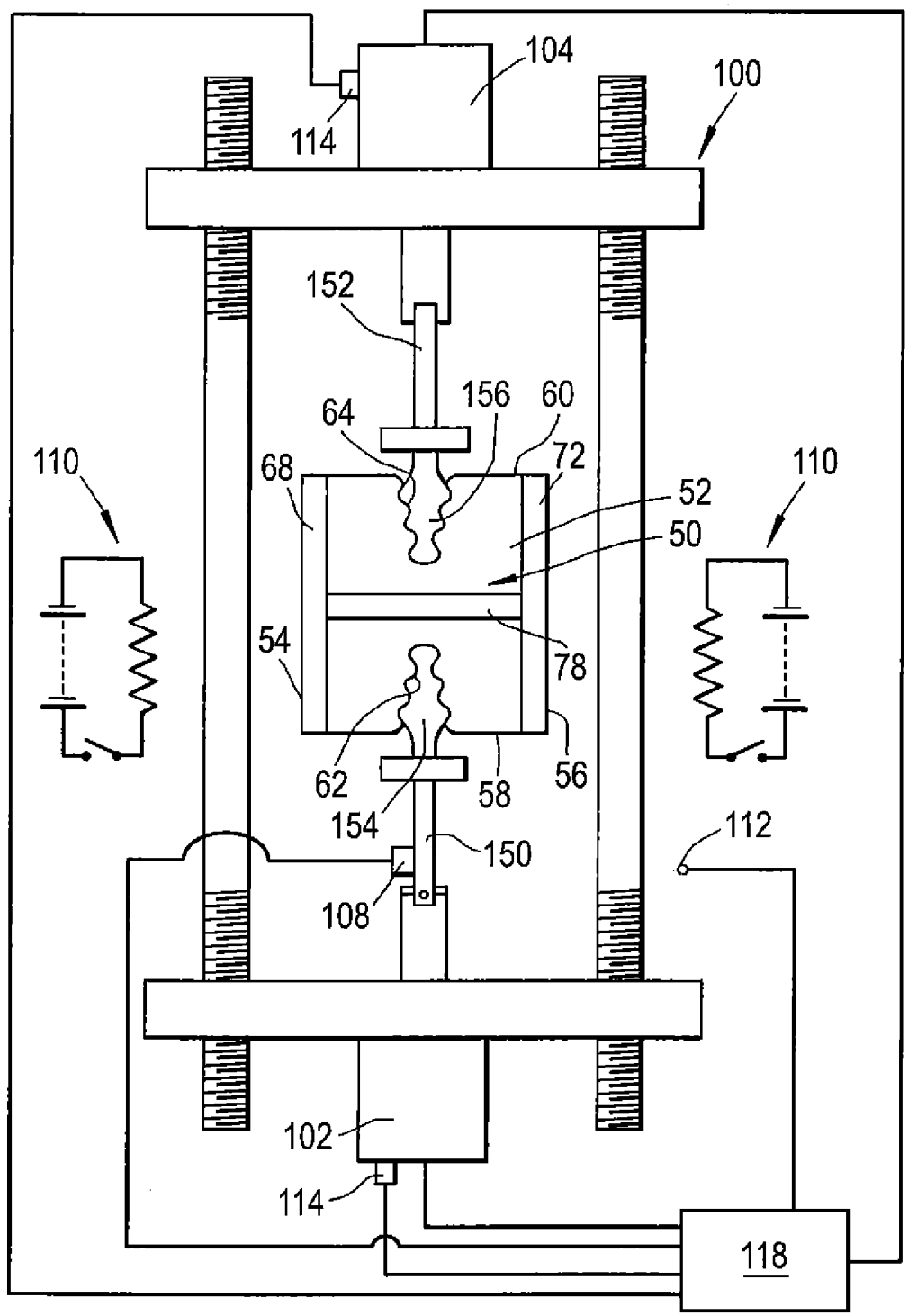
FIG. 7 is an apparatus for fatigue testing the disc post specimen in FIG. 4.

Finally the specimen 50 is fatigue tested using a fatigue testing machine 100 shown in FIG. 7 to determine the fatigue life of the specimen 50 and/or to understand the growth of the channel 84 and/or to predict the rate of growth of the channel 84 after a given number of corrosion-fatigue cycles.

The fatigue testing machine 100 comprises a first loading device 102 and a second loading device 104 which are arranged to apply tensile loads on a first attachment member 150 and a second attachment member 152. The first and second attachment members 150 and 152 have corresponding firtree shaped roots 154 and 156 which locate in the firtree shaped slots 62 and 64 in the specimen 50. The first and second loading device 102 and 104 are thus arranged to apply a tension load on the first and second attachment members 150 and 152 and the specimen 50. The first and second loading devices 102 and 104 may comprise a conventional load cell capable of applying tensile loads of up to several hundred kN, e.g. 200 kN. A vibration device 108 is provided to vibrate the first and second attachment members 150 and 152 and the specimen 50. The vibration device 108 for example comprises a piezoelectric transducer, a magnetostrictive transducer or mechanical shaker or other suitable device acoustically coupled to the first attachment member 10. A heating device 110 is provided to heat the first and second attachment members 150 and 152 and the specimen 50, if testing is required at higher temperatures. There are temperature sensors 112, displacement sensors 114, force sensors 116 etc to measure temperature, displacement and force and these are stored in a processor 118. The temperature, displacement and force sensors are standard sensors. The processor 118 also controls the first and second loading devices 102 and 104, the heating device 110 and the vibration device 108. The fatigue testing machine 100 may also be provided with a surrounding atmosphere of air or a surrounding corrosive atmosphere of air and sulphur dioxide.

EXAMPLE 1

A channel of suitable depth and width is machined into a surface of the tooth of the firtree of the disc post of the specimen 50. The salt solution is supplied into the channel 84 in the surface 82 of the specimen 50 and the specimen 50 is heated to 200° C. to evaporate the solvent from the salt solution to deposit the salt in the channel 84 in the surface 82 of the specimen 50. The specimen 50 is placed in an atmosphere containing air and sulphur dioxide for a period of 50 hours at 700° C. to partially precondition the grain boundaries of the specimen 50. The specimen 50 is removed from the atmosphere of air and sulphur dioxide. More salt solution is supplied into the channel 84 in the surface 82 of the specimen 50 and the specimen 50 is heated to 200° C. to evaporate the solvent from the salt solution to deposit the salt in the channel 84 in the surface 82 of the specimen 50. The specimen 50 is placed in the atmosphere containing air and sulphur dioxide for a period of 50 hours at 700° C. to partially precondition the grain boundaries of the specimen 50. The steps of supplying salt solution into the channel 84 and evaporating the solvent to deposit the salt into the channel 84 and placing the specimen 50 into the atmosphere of air and sulphur dioxide for 50 hours are then repeated until the total amount of time the specimen 50 has spent in the atmosphere of air and sulphur dioxide is 300 hours. Then the specimen 50 is placed in the fatigue testing machine in air and tested to failure to assess the remnant life of the specimen 50.

EXAMPLE 2

A channel of suitable depth and width is machined into a surface of the tooth of the firtree of the disc post of the specimen 50. The salt solution is supplied into the channel 84 in the surface 82 of the specimen 50 and the specimen 50 is heated to 200° C. to evaporate the solvent from the salt solution to deposit the salt in the channel 84 in the surface 82 of the specimen 50. The specimen 50 is placed in an atmosphere containing air and sulphur dioxide for a period of 50 hours at 700° C. to partially precondition the grain boundaries of the specimen 50. The specimen 50 is removed from the atmosphere of air and sulphur dioxide. More salt solution is supplied into the channel 84 in the surface 82 of the specimen 50 and the specimen 50 is heated to 200° C. to evaporate the solvent from the salt solution to deposit the salt in the channel 84 in the surface 82 of the specimen 50. The specimen 50 is placed in the atmosphere containing air and sulphur dioxide for a period of 50 hours at 700° C. to partially precondition the grain boundaries of the specimen 50. The steps of supplying salt solution into the channel 84 and evaporating the solvent to deposit the salt into the channel 84 and placing the specimen 50 into the atmosphere of air and sulphur dioxide for 50 hours are then repeated until the total amount of time the specimen 50 has spent in the atmosphere of air and sulphur dioxide is 300 hours. Then the specimen 50 is placed in the fatigue testing machine in a corrosive atmosphere of air and sulphur dioxide and tested to failure to assess the remnant life of the specimen 50.

EXAMPLE 3

A channel of suitable depth and width is machined into a surface of the tooth of the firtree of the disc post of the specimen 50. The salt solution is supplied into the channel 84 in the surface 82 of the specimen 50 and the specimen 50 is heated to 200° C. to evaporate the solvent from the salt solution to deposit the salt in the channel 84 in the surface 82 of the specimen 50. The specimen 50 is placed in an atmosphere containing air and sulphur dioxide for a period of 50 hours at 700° C. to partially precondition the grain boundaries of the specimen 50. The specimen 50 is removed from the atmosphere of air and sulphur dioxide. More salt solution is supplied into the channel 84 in the surface 82 of the specimen 50 and the specimen 50 is heated to 200° C. to evaporate the solvent from the salt solution to deposit the salt in the channel 84 in the surface 82 of the specimen 50. The specimen 50 is placed in the atmosphere containing air and sulphur dioxide for a period of 50 hours at 700° C. to partially precondition the grain boundaries of the specimen 50. The steps of supplying salt solution into the channel 84 and evaporating the solvent to deposit the salt into the channel 84 and placing the specimen 50 into the atmosphere of air and sulphur dioxide for 50 hours are then repeated until the total amount of time the specimen 50 has spent in the atmosphere of air and sulphur dioxide is 300 hours. More salt solution is supplied into the channel 84 in the surface 82 of the specimen 50 and the specimen 50 is heated to 200° C. to evaporate the solvent from the salt solution to deposit the salt in the channel 84 in the surface 82 of the specimen 50. Then the specimen 50 is placed in the fatigue testing machine in a corrosive atmosphere of air and sulphur dioxide. The specimen 50 is subjected to a number of cycles of increasing the stress on the specimen 50 from zero to a maximum stress, holding at the maximum stress for a preselected period of time and then reducing the stress to zero while within the corrosive atmosphere and then examining the specimen 50 to understand the growth of the channel 84 and/or to predict the rate of growth of the channel 84 after a given number of corrosion-fatigue cycles. For example the specimen 50 may be subject to 1000 cycles, 2000 cycles and 4000 cycles and examined after each to understand the growth of the channel 84 and/or to predict the rate of growth of the channel 84 after a given number of corrosion-fatigue cycles.

EXAMPLE 4

A channel of suitable depth and width is machined into a surface of the tooth of the firtree of the disc post of the specimen 50. The salt solution is supplied into the channel 84 in the surface 82 of the specimen 50 and the specimen 50 is heated to 200° C. to evaporate the solvent from the salt solution to deposit the salt in the channel 84 in the surface 82 of the specimen 50. The specimen 50 is placed in an atmosphere containing air and sulphur dioxide for a period of 50 hours at 700° C. to partially precondition the grain boundaries of the specimen 50. The specimen 50 is removed from the atmosphere of air and sulphur dioxide. More salt solution is supplied into the channel 84 in the surface 82 of the specimen 50 and the specimen 50 is heated to 200° C. to evaporate the solvent from the salt solution to deposit the salt in the channel 84 in the surface 82 of the specimen 50. The specimen 50 is placed in the atmosphere containing air and sulphur dioxide for a period of 50 hours at 700° C. to partially precondition the grain boundaries of the specimen 50. The steps of supplying salt solution into the channel 84 and evaporating the solvent to deposit the salt into the channel 84 and placing the specimen 50 into the atmosphere of air and sulphur dioxide for 50 hours are then repeated until the total amount of time the specimen 50 has spent in the atmosphere of air and sulphur dioxide is 300 hours. More salt solution is supplied into the channel 84 in the surface 82 of the specimen 50 and the specimen 50 is heated to 200° C. to evaporate the solvent from the salt solution to deposit the salt in the channel 84 in the surface 82 of the specimen 50. Then the specimen 50 is placed in the fatigue testing machine in a corrosive atmosphere of air and sulphur dioxide. The specimen 50 is subjected to cycles of increasing the stress on the specimen 50 from zero to a maximum stress, holding at the maximum stress for a preselected period of time and then reducing the stress to zero while within the corrosive atmosphere and tested to failure to assess the remnant life of the specimen 50. Further amounts of salt solution are supplied into the channel 84 after periods of time of 50 hours. This provides data for the safe service limit, safe service life, of corrosion-fatigue for the corresponding component of the gas turbine engine.

The fatigue testing machine 60 may perform low cycle fatigue testing, high cycle fatigue testing of the specimen 50 and may comprise applying tension loads to the specimen 50.

Figure 6:
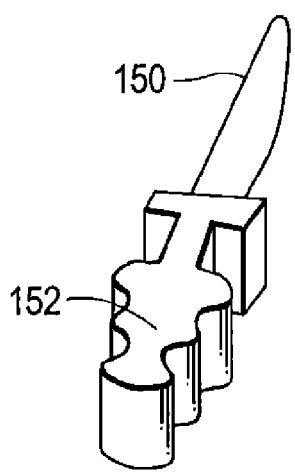
FIG. 6 is a perspective view of a rotor blade specimen.

FIG. 6 shows the first attachment member 150. The first attachment member 150 may be used as the specimen in which case a channel would be machined in the root 152 of the first attachment member 150 and the salt solution applied to the channel and any one of the fatigue testing procedures described above may be used.

Although the present invention has been described with reference to fatigue testing of specimens having the shape of a gas turbine engine disc post, it is equally applicable to fatigue testing of specimens having the shape of other gas turbine engine components or components of other engines, machines or apparatus, for example turbine blades, compressor blades, shafts, discs etc, in particular a rotor blade root, e.g. a turbine blade root or a compressor blade root. The rotor blade root may have a firtree shape or a dovetail shape. Although the present invention has been described with reference to fatigue testing of nickel based superalloys it is also applicable to fatigue testing of other superalloys and other alloys.

Currently remnant fatigue life data is obtained by carrying out fatigue testing on components removed from a gas turbine engine. Thus, currently only remnant fatigue life data corresponding to the age of the oldest gas turbine engines in service is available.

The advantage of the present invention is that by machining a channel in a component and pre-conditioning the component using the salt solution and heat treatment it is possible to predict, or determine, the remnant fatigue life of a component having a deep feature in a surface of the component before a deep feature is produced in actual component of a gas turbine engine during engine service due to hot corrosion. The specimens may be used for pre-conditioning of the grain boundaries and then fatigue testing or may be used to aid the continued growth of a corrosion fatigue feature in situ to understand the conditions necessary to transition from environmentally assisted mechanical cracking. Thus, the likely amount, e.g. depth, of corrosion after particular periods of time of a component may be predicted. If it is predicted that a component will have a significant reduction in fatigue life, then it is possible to remove and replace that particular component with a new component or a refurbished component.

The provision of a channel in the surface of the component, specimen, is controllable. The channel may be easily placed in a real engine component to enable accurate loads to be placed on the component to determine the remnant fatigue life of the component.

The invention claimed is:

1. A method of fatigue testing a component comprising the steps of:
   a) providing a component having a surface and machining a channel of predetermined depth and predetermined width in the surface of the component such that the channel has a closed bottom, a first side, and a second side and is open at the surface of the component,
   b) applying a salt solution into the channel in the surface of the component and heating the component to a suitable temperature to evaporate the solvent from the salt solution to deposit the salt in the channel in the surface of the component,
   c) placing the component in a corrosive atmosphere for a predetermined period of time at a predetermined temperature to precondition the grain boundaries, and
   d) fatigue testing the component.

2. A method as claimed in claim 1 wherein
step b) comprises heating the component to 200° C. and applying salt solution at a rate of 0.25 µg/cm$^2$/hr to 10 µg/cm$^2$/hr.

3. A method as claimed in claim 1 wherein
the corrosive atmosphere in step c) comprises air and sulphur dioxide.

4. A method as claimed in claim 1 wherein
the predetermined period of time in step c) is 50 to 500 hours.

5. A method as claimed in claim 4 wherein
the predetermined period of time in step c) is 300 hours.

6. A method as claimed in claim 1 wherein
the predetermined temperature in step c) is 600° C. to 750° C.

7. A method as claimed in claim 1 wherein
step d) comprises fatigue testing in air.

8. A method as claimed in claim 1 wherein
step d) comprises fatigue testing in a corrosive atmosphere.

9. A method as claimed in claim 8 wherein
step d) comprises fatigue testing in air and sulphur dioxide.

10. A method as claimed in claim 1 wherein
step d) comprises fatigue testing to determine the remnant life of the component.

11. A method as claimed in claim 1 wherein
step d) comprises repeatedly applying a salt solution into the channel in the surface of the component and heating the component to a suitable temperature to evaporate the solvent from the salt solution to deposit the salt in the channel in the surface of the component and placing the component in a corrosive atmosphere at a predetermined temperature for predetermined periods of time while fatigue testing the component to determine the remnant life of the component.

12. A method as claimed in claim 11 wherein
the corrosive atmosphere comprises air and sulphur dioxide.

13. A method as claimed in claim 11 wherein
the predetermined temperature is 600° C. to 750° C.

14. A method as claimed in claim 1 wherein
step d) comprises applying a salt solution into the channel in the surface of the component and heating the component to a suitable temperature to evaporate the solvent from the salt solution to deposit the salt in the channel in the surface of the component and placing the component in a corrosive atmosphere at a predetermined temperature and stopping the fatigue testing after predetermined numbers of cycles, examining the component and predicting the rate of growth of the channel after a given number of fatigue cycles.

15. A method as claimed in claim 14 wherein
the corrosive atmosphere comprises air and sulphur dioxide.

16. A method as claimed in claim 14 wherein
the predetermined temperature is 600° C. to 750° C.

17. A method as claimed in claim 1 wherein
the component comprises a specimen having a shape selected from the group consisting of a gas turbine engine rotor disc post and a rotor blade root.

18. A method as claimed in claim 17 wherein
the component has a shape selected from the group consisting of a firtree shape and a dovetail shape.

19. A method as claimed in claim 18 wherein
step a) comprises machining the channel in an edge of bedding region of a tooth of the firtree shape disc post.

20. A method as claimed in claim 1 wherein
step a) comprises electro-discharge machining the channel of predetermined depth and predetermined width in a surface of a component.

21. A method as claimed in claim 1 wherein
step d) is selected from the group consisting of low cycle fatigue testing and high cycle fatigue testing.

22. A method as claimed in claim 1 wherein
the salt consist of sodium sulphate and sodium chloride.

23. A method as claimed in claim 22 wherein the salts consists of 98% sodium sulphate and 2% sodium chloride.

24. A method as claimed in claim 1 wherein step d) comprises predicting the rate of growth of the channel.

25. A method as claimed in claim 1 wherein step d) comprises applying a tensile load.

26. A method as claimed in claim 1 wherein step d) comprises arranging the surface of the component to abut a surface of a correspondingly shaped component.

27. A method of fatigue testing a superalloy component comprising the steps of:
   a) machining a channel of predetermined depth and predetermined width in a surface of a superalloy component,
   b) applying a salt solution into the channel in the surface of the component and heating the component to a suitable temperature to evaporate the solvent from the salt solution to deposit the salt in the channel in the surface of the component, applying the salt solution at a rate of $0.25 \mu g/cm^2/hr$ to $10 \mu g/cm^2/hr$,
   c) placing the component in a corrosive atmosphere for a predetermined period of time at a predetermined temperature to precondition the grain boundaries, the predetermined temperature being 600° C. to 750° C., repeating steps b) and c) a predetermined number of times, and
   d) fatigue testing the component.

28. A method of fatigue testing a nickel base superalloy component comprising the steps of:
   a) machining a channel of predetermined depth and predetermined width in a surface of a nickel base superalloy component,
   b) applying a salt solution into the channel in the surface of the component and heating the component to a suitable temperature to evaporate the solvent from the salt solution to deposit the salt in the channel in the surface of the component, the salt solution consisting of sodium sulphate and sodium chloride, applying the salt solution at a rate of $0.25 \mu g/cm^2/hr$ to $10 \mu g/cm^2/hr$,
   c) placing the component in a corrosive atmosphere for a predetermined period of time at a predetermined temperature to precondition the grain boundaries, the corrosive atmosphere comprising air and sulphur dioxide, the predetermined temperature being 600° C. to 750° C., repeating steps b) and c) a predetermined number of times, and
   d) fatigue testing the component.

* * * * *